US011925677B2

(12) United States Patent
Williams

(10) Patent No.: US 11,925,677 B2
(45) Date of Patent: Mar. 12, 2024

(54) TREATMENT OF DIABETES AND CHRONIC PANCREATITIS USING BOTULINUM TOXIN

(71) Applicant: Penland Foundation, Beaumont, TX (US)

(72) Inventor: Roland M. Williams, Beaumont, TX (US)

(73) Assignee: Penland Foundation, Beaumont, TX (US)

( * ) Notice: Subject to any disclaimer, the term of this patent is extended or adjusted under 35 U.S.C. 154(b) by 0 days.

(21) Appl. No.: 17/862,282

(22) Filed: Jul. 11, 2022

(65) Prior Publication Data

US 2023/0011705 A1    Jan. 12, 2023

Related U.S. Application Data

(60) Provisional application No. 63/220,960, filed on Jul. 12, 2021.

(51) Int. Cl.
*A61K 38/48* (2006.01)
*A61K 9/00* (2006.01)
*A61P 3/10* (2006.01)

(52) U.S. Cl.
CPC ........ *A61K 38/4893* (2013.01); *A61K 9/0019* (2013.01); *A61P 3/10* (2018.01)

(58) Field of Classification Search
CPC .................................................. A61K 38/4893
See application file for complete search history.

(56) References Cited

U.S. PATENT DOCUMENTS

| 5,766,605 | A | 6/1998 | Sanders et al. |
| 6,063,768 | A | 5/2000 | First |
| 6,139,845 | A | 10/2000 | Donovan |
| 6,143,306 | A | 11/2000 | Donovan |
| 6,261,572 | B1 | 7/2001 | Donovan |
| 6,337,075 | B1* | 1/2002 | Donovan ................. A61P 1/18 424/832 |
| 6,632,440 | B1 | 10/2003 | Quinn et al. |
| 6,977,080 | B1 | 12/2005 | Donovan |
| 7,655,244 | B2 | 2/2010 | Blumenfeld |
| 8,470,337 | B2 | 6/2013 | Manack et al. |
| 8,734,810 | B2 | 5/2014 | Blumenfeld |
| 8,852,163 | B2 | 10/2014 | Deem et al. |
| 8,972,004 | B2 | 3/2015 | Simon et al. |
| 9,254,314 | B2 | 2/2016 | Finzi et al. |
| 9,707,207 | B2 | 7/2017 | Finegold |
| 10,011,823 | B2 | 7/2018 | Barbieri et al. |
| 10,258,673 | B2 | 4/2019 | Pokushalov et al. |
| 10,722,552 | B1 | 7/2020 | Williams |
| 10,960,061 | B1 | 3/2021 | Williams |
| 10,973,873 | B1 | 4/2021 | Williams |
| 10,987,441 | B1 | 4/2021 | Sykes |
| 2001/0012828 | A1 | 8/2001 | Aoki et al. |
| 2004/0062776 | A1 | 4/2004 | Voet |
| 2004/0213815 | A1 | 10/2004 | Ackerman |
| 2004/0220544 | A1 | 11/2004 | Heruth et al. |
| 2005/0147626 | A1* | 7/2005 | Blumenfeld ............ A61P 25/04 424/239.1 |
| 2005/0191320 | A1 | 9/2005 | Turkel et al. |
| 2007/0259002 | A1 | 11/2007 | Batchelor |
| 2009/0142430 | A1 | 6/2009 | Sanders et al. |
| 2009/0232850 | A1* | 9/2009 | Manack ............... A61K 38/164 424/239.1 |
| 2010/0222286 | A1 | 9/2010 | Ip et al. |
| 2010/0303788 | A1 | 12/2010 | Francis et al. |
| 2011/0200639 | A1 | 8/2011 | Blumenfeld |
| 2012/0093827 | A1 | 4/2012 | Van Schaack et al. |
| 2012/0195878 | A1 | 8/2012 | Haag-Molkenteller et al. |
| 2012/0244188 | A1 | 9/2012 | Blumenfeld et al. |
| 2012/0251519 | A1 | 10/2012 | Blumenfeld et al. |
| 2013/0251830 | A1 | 9/2013 | Manack et al. |
| 2014/0099298 | A1* | 4/2014 | Blumenfeld ....... A61K 38/4893 424/94.67 |
| 2015/0086533 | A1 | 3/2015 | Borodic |
| 2016/0095908 | A1 | 4/2016 | Borodic et al. |
| 2017/0173123 | A1 | 6/2017 | Blumenfeld |
| 2017/0333537 | A9 | 11/2017 | Borodic |
| 2018/0071361 | A1 | 3/2018 | Abiad et al. |
| 2019/0038646 | A1 | 2/2019 | Bright et al. |
| 2019/0300583 | A1 | 10/2019 | Jarpe et al. |
| 2020/0239528 | A1 | 7/2020 | Binz et al. |

(Continued)

FOREIGN PATENT DOCUMENTS

| AU | 2013202878 | 5/2013 |
| EP | 2072039 A1 | 6/2009 |

(Continued)

OTHER PUBLICATIONS

Strobl et al., Toxins, 2015; 7: 1629-1648 (Year: 2015).*

(Continued)

*Primary Examiner* — Brian Gangle
*Assistant Examiner* — Lakia J Jackson-Tongue
(74) *Attorney, Agent, or Firm* — Fox Rothschild LLP

(57) ABSTRACT

A method for treating chronic pancreatitis and diabetes type II in a patient in need thereof comprises administering botulinum toxin to the patient. The botulinum toxin may be administered by subcutaneous or intradermal injection. The subcutaneous or intradermal injection may be administered to and/or around the vicinity of a trigeminal nerve, a cervical nerve, a thoracic nerve, a lumbar nerve, a sacral nerve, or a combination thereof.

20 Claims, No Drawings

(56) References Cited

U.S. PATENT DOCUMENTS

| | | | | |
|---|---|---|---|---|
| 2021/0060144 | A1* | 3/2021 | Brooks | A61P 25/06 |
| 2021/0187063 | A1 | 6/2021 | Williams | |
| 2022/0143158 | A1* | 5/2022 | Abumrad | A61P 3/10 |

FOREIGN PATENT DOCUMENTS

| | | |
|---|---|---|
| JP | 2007509953 A | 4/2007 |
| JP | 2012107051 A | 6/2012 |
| KR | 20100032982 A | 3/2010 |
| KR | 20150126979 A | 11/2015 |
| WO | 95/28171 A1 | 10/1995 |
| WO | 00/10598 A2 | 3/2000 |
| WO | 2005072433 | 8/2005 |
| WO | 2010013495 A1 | 2/2010 |
| WO | 2011084507 A1 | 7/2011 |
| WO | 2012134897 A1 | 10/2012 |
| WO | 2014184746 A1 | 11/2014 |
| WO | 2018172264 A1 | 9/2018 |
| WO | 2019126542 A1 | 6/2019 |
| WO | 2019145577 A1 | 8/2019 |
| WO | 2020110458 A1 | 6/2020 |
| WO | WO 2022/183064 A1 * | 2/2021 |

OTHER PUBLICATIONS

Park et al., Toxins 2017, 9, 260:1-15 (Year: 2017).*
Herner et al., Int J Cancer, 2011; 129(10):2349-59 (Year: 2011).*
Mayo Clinic, https://www.mayoclinic.org/diseases-conditions/epilepsy/diagnosis-treatment/drc-20350098; accessed on Sep. 20, 2022 (Year: 2022).*
Sarawagi, Sec. Molecular Psychiatry, 2021; 12(637863): 1-16 (Year: 2021).*
Hart et al., Am J Gastroenterol. Jan. 2020 ; 115(1): 49-55 (Year: 2020).*
Ristic, https://supplements.selfdecode.com/blog/substance-p-roles/ (Year: 2022).*
Wang et al., Frontiers in Neuroscience, 2020; 14:1-12 (Year: 2020).*
Farnsworth, Medical News Today, 2022; Glutamate: Function and healthy levels (medicalnewstoday.com) (Year: 2022).*
Cleveland Clinic—Glutamate; https://my.clevelandclinic.org/health/articles/22839-glutamate (Year: 2023).*
Advance Nursing, "Angle of Injection," available online at: <https://nursing-skills.blogspot.com/2014/01/angle-of-injection.html>, 2 pages (2020).
Chien et al., "Sympathetic Fiber Sprouting in Chronically Compressed Dorsal Root Ganglia Without Peripheral Axotomy," Author manuscript, published in final form as: J. Neuropathic Pain Symptom Palliation, 1(1), pp. 19-23, 7 pages (2005).
Children's Hospital of Pittsburgh, "Cirrhosis in Children: Symptoms and Treatment," available online at: <https://www.chp.edu/our-services/transplanUliver/education/liver-disease-states/cirrhosis>, 4 pages (2020).
Diel et al., "Photophobia and sensations of dryness in migraine patients occur independent of baseline tear volume and improve following botulinum toxin A injections," Author manuscript, published in final form as: Br. J. Ophthalmol., 103(8), pp. 1024-1029, 15 pages (2019).
Dobrek and Thor, "Glutamate NMDA Receptors in Pathophysiology and Pharmacotherapy of Selected Nervous System Dseases," Postepy Hig Med Dosw (online), 65, pp. 338-346 (2011).
Doherty, "The Link Between Migraines and Tinnitus, Buzzing or ringing in your ears could be related to your episodes," available online at: https://www.verywellhealth.com/link-between-migraines-and-tinnitus-4077631>, 13 pages (2019).
Espinosa-Sanchez and Lopez-Escamez, "New insights into pathophysiology of vestibular migraine," Frontiers in Neurology, 6(12), pp. 1-6 (2015).
Fernandez-Rodriguez et al., "Plasma Levels of Substance P in Liver Cirrhosis: Relationship to the Activation of Vasopressor Systems and Urinary Sodium Excretion," Hepatology, 21, pp. 35-40 (1995).
Fleischmann et al., "Nitrous oxide may not increase the risk of cancer recurrence after colorectal surgery: a follow-up of a randomized controlled trial" BMC Anesthesiology, 9 pages (2009).
Glatte et al., "Architecture of the Cutaneous Autonomic Nervous System," Frontiers in Neurology, 10(970), pp. 1-11 (2019).
Harley Academy, "Understanding Different Types of Botulinum Toxin A," 5 pages (2021).
Hart et al., "Chronic Pancreatitis: Managing a Difficult Disease," Am. J. Gastroenterol., 115(1), pp. 49-55 (2020).
Harvard Health Publishing, "Cardiac Arrhythmias, What is it?" available online at: <https://www.health.harvard.edu/a_to_z/cardiac-arrhythmias-a-to-z>; 5 pages (2019).
Hulme and Snowling, "Reading disorders and dyslexia," Curr. Opin. Pediatr., 28, pp. 731-735 (2016).
Kumar, "The Emerging Role of Botulinum Toxin In The Treatment of Orofacial Disorders: Literature Update," Asian J. Pharm. Clin. Res., 10(9), pp. 21-29 (2017).
LeWitt and Trosch, "Idiosyncratic Adverse Reactions to Intramuscular Botulinum Toxin Type A Injection," Movement Disorders, 12(6), pp. 1054-1067 (1997).
Lim and Sheet, "Botulinum toxin, Quo Vadis?," Medical Hypotheses, 69, pp. 718-723 (2007).
Mayo Clinic, "Autism Spectrum Disorder," available online at: <https://www.mayoclinic.org/diseases-conditions/autism-spectrum-disorder/symptoms-causes/syc-20352928?p=1, 5 pages (2019).
Mazzone and Undem, "Vagal Afferent Innervation of the Airways in Health and Disease," Physiol. Rev., 96, pp. 975-1024 (2016).
Mitchell and Borasio, "Amyotrophic lateral sclerosis," Lancet 369: pp. 2031-2041 (2007).
Monroy et al., "The Use of Botulinum Toxin-A in the Treatment of Severe Bruxism in a Patient with Autism: A Case Report," Special Care in Dentistry, 26(1), pp. 37-39 (2006).
Mortazavi et al., "Xerostomia Due to Systemic Disease: A Review of 20 Conditions and Mechanisms," Ann. Med. Health Sci. Res., 4(4), pp. 503-510 (2014).
Nair et al., "Impaired thalamocortical connectivity in autism spectrum disorder: a study of functional and anatomical connectivity," Brain, A Journal of Neurology, 136, pp. 1942-1955 (2013).
National Istitutes of Health "Juvenile Amyotrophic Lateral Sclerosis," found online at: <https://rarediseases.info.nih.govtdiseasesi11901/juvenile- amyotrophic-lateral-sclerosis>, 8 pages (2020).
Oomens and Forouzanfar, "Pharmaceutical Management of Trigeminal Neuralgia in the Elderly," Drugs Aging, 32, pp. 717-726 (2015).
Panju et al., "Atypical Sympathetic Arousal In Children with Autism Spectrum Disorder and Its Association with Anxiety Symptomatology," Molecular Autism, 6(64), 10 pages (2015).
Powell et al., "The Role of CGRP in Tile Development of Morphine Tolerance and Physical Dependence," 4th International Meeting on Calcitonin Gene-Related Peptide (CGRP), The Scientific World 1(S1), 1 page (2001).
Pugh et al., "Glutamate and choline levels predict individual differences in reading ability in emergent readers," J. Neurosci., 34(11), pp. 4082-4089 (2014).
Ristic, "7 Proven Roles of Substance P and Its Associated Diseases," available online at: https://supplements.selfdecode.com/blog/substance-p-roles/>, 9 pages (2021).
Rojas, "The role of glutamate and its receptors in autism and the use of glutamate receptor antagonists in treatment," Author manuscript, published in final form as: J. Neural. Transm., 121(8), pp. 891-905 (2014 ).
Sadick, "Botulinum toxin type B," (Abstract) Dermatol. Surg., 29(4), pp. 348-350 (2003).
Sarawagi et al., "Glutamate and GABA Homeostasis and Neurometabolism in Major Depressive Disorder," Frontiers in Psychiatry, 12(637863), pp. 1-16 (2021).
Saunte and Christensen, "Improvement in readingsymptoms followingbotulinum toxin A injectionfor convergenceinsufficiency typeintermittent exotropia," Acta Opthalmologica 93(5), pp. e391-e392 (2015).
Scott and Fryer, "Role of Parasympathetic Nerves and Muscarinic Receptors in Allergy and Asthma," Author manuscript, published in final form as: Chem. Immunol. Allergy, 98: pp. 48-69 (2012).

(56) References Cited

OTHER PUBLICATIONS

Shimmura et al., "Alteration of Plasma Glutamate and Glutamine Levels in Children with High-Functioning Autism," PLoS ONE, 6(10), 6 pages (2011).
Smith, "Hyperhidrosis," Vascular Surgery, 31(5), pp. 251-255 (2015).
Squires et al., "The Use of Botulinum Toxin Injections to Manage Drooling in Amyotrophic Lateral Sclerosis/Motor Neurone Disease: A Systematic Review," Dysphagia, 29, pp. 500-508 (2014).
Trizna, "Dermatologic Use of Botulinum Toxin," available online at emedicine.medscape.com; 10 pages (2019).
Vacca et al., "Botulinum toxin A increases analgesic effects of morphine, counters development of morphine tolerance and modulates glia activation and µ opiod receptor expression in neuropathic mice," Brain, Behavior, and Immunity, 32, pp. 40-50 (2013).
Veenstra-Vanderweele et al., "Arbaclofen in Children and Adolescents with Autism Spectrum Disorder: A Randomized, Controlled, Phase 2 Trial," Neuropsychopharmacology, 42, pp. 1390-1398 (2017).
WebMD, "ADHD and Dyslexia: How to Tell Them Apart," available online at: <https://www.webmd.com/add-adhd/adhd-dyslexia-tell-apart?print=true>, 3 pages (2020).
WebMD, "Treatments for Dyslexia," available online at: <https://www.webmd.com/children/dyslexia-treatments?print=true>, 1 page (2020).
What-When-How, "Neuroscience," available online at: <http://what-when-how.com/neuroscience> 2 pages (2020).
Wijesekera and Leigh, "Amyotrophic lateral sclerosis," Orphanet Journal of Rare Diseases, 4(3), 22 pages (2009).
Niebroj-Dobosz and Janik, "Amino acids acting as transmitters in amyotrophic lateral sclerosis (ALS)," Acta Neural. Scand., 100, pp. 6-11 (1999).
Nemmi et al., "Connectivity of the Human Number Form Area Reveals Development of a Cortical Network forMathematics," Front. Hum. Neurosci. (2018).
Morin, "Reading skills at different ages," 3 pages, Retrieved Online: https://www.understood.org/en/articles/reading-skills-what-to-expect-at- different-ages (2014).
Shonkoff JP, Phillips DA, editors "From Neurons to Neighborhoods: The Science of Early Childhood Development", National Research Council (US) and Institute of Medicine (US) Committee on Integrating the Science of Early Childhood Development, 25 pages (2000), Ch. 8: The Developing Brain.
Antonucci et al., "SNAP-25 a Known Presynaptic Protein with Emerging Postsynaptic Functions," Frontiers in Synaptic Neuroscience, 9 pages (2016).
U.S. Appl. No. 17/880,962, filed Aug. 4, 2022, Botulinum Toxin for Use in Treatment.
U.S. Appl. No. 17/204,922, filed Mar. 17, 2021, Treatment of Dyslexia Using Botulinum Toxin.
U.S. Appl. No. 17/987,549, filed Nov. 15, 2022, Treatment of Asthma Using Botulinum Toxin.
U.S. Appl. No. 17/987,626, filed Nov. 15, 2022, Treatment of Chronic Obstructive Pulmonary Disease Using Botulinum Toxin.
U.S. Appl. No. 17/987,653, filed Nov. 15, 2022, Treatment of Cardiac Arrhythmia Using Botulinum Toxin.
U.S. Appl. No. 17/215,082, filed Mar. 29, 2021, Treatment of Amyotrophic Lateral Sclerosis Using Botulinum Toxin.
U.S. Appl. No. 17/987,675, filed Nov. 15, 2022, Treatment of Cirrhosis Using Botulinum Toxin.
U.S. Appl. No. 17/862,295, filed Jul. 11, 2022, Treatment of Acute and Chronic Kidney Disease.
U.S. Appl. No. 16/657,933, filed Oct. 18, 2019, Treatment of Autism Using Botulinum Toxin.
U.S. Appl. No. 17/525,367, filed Nov. 12, 2021, Botulinum Toxin for Use In Treatment of Autism Spectrum Disorders.
U.S. Appl. No. 16/995,042, filed Aug. 17, 2020, Treatment Methods Using Botulinum Toxin.
U.S. Appl. No. 16/875,912, filed May 15, 2020, Treatment of Dyslexia Using Botulinum Toxin.
U.S. Appl. No. 16/875,924, filed May 15, 2020, Treatment of Asthma Using Botulinum Toxin.
U.S. Appl. No. 16/875,935, filed May 15, 2020, Treatment of Chronic Obstructive Pulmonary Disease Using Botulinum Toxin.
U.S. Appl. No. 16/875,945, filed May 15, 2020, Treatment of Cardiac Arrhythmia Using Botulinum Toxin.
U.S. Appl. No. 16/875,947, filed May 15, 2020, Treatment of Amyotrophic Lateral Sclerosis Using Botulinum Toxin.
U.S. Appl. No. 16/875,951, filed May 15, 2020, Treatment of Cirrhosis Using Botulinum Toxin.

\* cited by examiner

TREATMENT OF DIABETES AND CHRONIC PANCREATITIS USING BOTULINUM TOXIN

PRIORITY CLAIM

The application is based on and claims priority to U.S. Provisional Application No. 63/220,960, filed Jul. 17 2021, the entirety of each which is incorporated by reference.

This application is also related by ownership to the following cases, filed on Oct. 18, 2019: TREATMENT OF AUTISM USING BOTULINUM TOXINS, Ser. No. 16/657,933, now U.S. Pat. No. 10,722,552; filed on Oct. 18, 2019: TREATMENT OF NARCOTICS TOLERANCE USING BOTULINUM TOXINS, Ser. No. 16/657,950, now abandoned; filed on Aug. 17, 2020: TREATMENT METHODS USING BOTULINUM TOXINS, Ser. No. 16/995,042, now U.S. Pat. No. 11,241,479; filed on May 15, 2020: TREATMENT OF DYSLEXIA USING BOTULINUM TOXIN, Ser. No. 16/875,912, now U.S. Pat. No. 10,967,052; filed on Aug. 17, 2020: TREATMENT OF ASTHMA USING BOTULINUM TOXIN, Ser. No. 16/995,042, now U.S. Pat. No. 11/241,479; filed on May 15, 2020: TREATMENT OF CHRONIC OBSTRUCTIVE PULMONARY DISEASE USING BOTULINUM TOXIN, Ser. No. 16/875,935, now U.S. Pat. No. 10/987,411; filed on May 15, 2020: TREATMENT OF CARDIAC ARRHYTHMIA USING BOTULINUM TOXIN, Ser. No. 16/875,945, now U.S. Pat. No. 10/960,060; filed on May 15, 2020: TREATMENT OF CIRRHOSIS USING BOTULINUM TOXIN, Ser. No. 16/875,951, now U.S. Pat. No. 11/090,371; filed on May 4, 2022: TREATMENT OF ARDS AND OTHER CONDITIONS CAUSED BY ACUTELY ELEVATED CYTOKINE LEVELS AND POST CARDS CHRONIC CYTOKINE PRODUCTION USING INHALED ANESTHETICS, Ser. No. 17/662,068.

TECHNICAL FIELD

Embodiments of the present disclosure generally relate to the treatment of the cause of chronic pancreatitis and diabetes. In particular, embodiments of the present disclosure are related to methods for treating, alleviating, and/or preventing chronic pancreatitis, which is caused by the pathological activation of the cytokine system. Embodiments of the present disclosure are also related to methods for treating, alleviating, and/or preventing diabetes caused by neurosignaling dysfunction in alpha and beta pancreatic cells that results in loss of central control of blood glucose levels.

Botulinum toxin and its mechanisms of action can lower exogenous substance P and glutamate levels and thereby their ability to chronically activate the cytokine system, interfere with normal central control of the glucose-regulating system in the pancreas, and cause neuro excitotoxicity damage or death in the beta cells.

BACKGROUND

It is well known that diabetes and chronic pancreatitis are very serious, chronic, medical conditions that develop in a significant number of human beings. The onset of the conditions can occur in a human being at an early age, although many times a person will not develop a condition until much later in life. In any event, the condition is quite debilitating unless treated, and often leads to complications in other medical conditions that a patient may have. Diabetes often advances the onset of medical conditions and ailments associated with aging and very often leads to complications in treating such conditions.

SUMMARY

The claimed disclosure is related to methods for treating chronic pancreatitis, diabetes type II, and other conditions that have resulted from excess production of substance P and glutamate, resulting in excess activation of the cytokine system, signaling dysfunction that results in elevated blood glucose levels, beta cell death, and insulin resistance in a patient in need thereof. Treatment involves the use of botulinum toxin to block only the overproduction of substance P and glutamate in the spinal and vagus sensory ganglia without affecting normal substance P and glutamate signaling.

BOTULINUM TOXIN

Botulinum toxin cleaves the SNAP25 and/or VAMP at the neuro muscular junction in muscles this causes the clinical effects of botulinum toxin. The resulting paralyzed muscles last for 3-4 months until the cell grows a new protein. This effect has been used for decades for overactive muscles (such as treating overactive muscles as part of cervical dystonia, blepharospasm, tic's, Parkinson's, cerebral palsy, wrinkles in the face, excessive sweating, and overactive bladder.)

In the sensory nerves, the mechanism has been used for treating migraines and depression. The effect of blocking the SNAP25 and/or VAMP in the glial, satellite, and astrocyte cells will work for 2-9 months until these cells grow new proteins. The important part of this mechanism is that the botulinum effect does not destroy cells and does not stop the normal production of or effects of acetylcholine (muscles) or substance P, CGRP, or glutamate in sensory nerves. These facts give huge advantages over a monoclonal antibody which would eliminate all glutamate, CGRP, and substance P. Side effects of such elimination would be disastrous. The receptor antagonists also have problems, because they are not site-specific, they block glutamate, substance P, and CGRP everywhere. Too little glutamate, substance P, and CGRP is a problem, as well as too much. It is difficult to regulate oral or I.V. doses to obtain the correct level of reduction in areas that are too high in glutamate, substance P, and/or CGRP without over-reduction in areas with normal levels.

Small doses of botulinum toxin injected into a specific muscle can deactivate the SNAP25 and/VAMP to calm the muscle's overreaction or paralyze the muscle temporarily if desired. If injected subcutaneously near unmyelinated sensory nerves, the botulinum toxin can stop the overproduction of the sensory neuro excitatory compounds without affecting normal glutamate, substance P, and CGRP production and function. It is, however, noted that botulinum toxin is highly lethal. Botulinum toxin is the most toxic poison known. One molecule of botulinum toxin destroys one protein molecule of SNAP25 and/or VAMP. A little bit goes a long way. Its production, storage, and injection must be done with knowledge and care.

In particular, the mechanism of the sensory effect (stopping overproduction of glutamate, substance P, and CGRP) is as follows: almost all nerves in the human body are surrounded by a protective coating called myelin, which protects the nerve and makes neural conduction faster. Botulinum toxin has difficulty penetrating the myelin. Just under the skin are sensory pain nerves called C-fibers, which are unmyelinated. Research has shown that very low doses of botulinum toxin can penetratethese axons and diffuse up theaxon to the cell body into the CSF and affect the SNAP25 and/or VAMP on the glial, satellite, and astrocyte cells. Subsequently, botulinum toxin destroys the SNAP25 and/or VAMP and prevents the release of the excess substance P, CGRP, and glutamate, which is involved in a response mechanism to neural injury without affecting normal glutamate, substance P, and CGRP production, use, or receptors. An example of the neural injury mechanism dysfunction is a shingles infection. The infection by the shingles virus damages the nerve but does not kill it, or there would be no feeling (numbness). This causes a spike in the production of glutamate, substance P, and CGRP. This causes the well-known shingles pain and hypersensitivity. Over a 2-3 month perod, the infection is controlled, the nerve heals, and the overproduction of the neuro excitatory chemicals gets back to normal. However, sometimes for unknown reasons, the overproduction does not get back to normal but remains high, and severe chronic pain and hypersensitivity persists. Chronically over stimulated neurons can cause numerous problems depending on where the neurons are located. The neuro excitatory chemicals can travel up the spinal cord to the brain in the CSF and affect neurons there. This process is called central sensitization. Depending on where glutamate, substance P, and CGRP are produced and where the molecules travel to, the molecules can cause chronic pain, headaches, vertigo, sensitivity to light, sensitivity to touch, cold sensitivity, overactive bladder, depression, anxiety, flashbacks, mental fogginess, vasoconstriction of extremities, and sleep disturbances.

DETAILED DESCRIPTION OF THE PREFERRED EMBODIMENTS

Further in relation to this, before explaining at least the preferred embodiments of the disclosure in greater detail, it is to be understood that the disclosure is not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined, the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, "consists essentially of" when used in conjunction with a composition means excluding other materials that contribute to mitigating cytokine overproduction, thereby treating pancreatitis, diabetes type II, and other conditions that have resulted from the overproduction of cytokines in the pancreas. The objective of administering botulinum toxin is to treat the conditions by mitigating cytokine overproduction. With the language, other materials that contribute to the treatment that materially affect the basic and novel characteristics of the disclosure are not required and are potentially counterproductive because they may offset the treatment effect of botulinum toxin. In other words, the meaning of "consists essentially of" is tied to the objective and excludes materials (that contribute to the treatment) that are pharmaceutically active for the treatment and materially mitigate cytokine overproduction and thereby affecting the treatment of the conditions. Small traces that have little or no effect to the treatment as part of the embodiments of the presentation disclosure may exist in a composition that consists essentially of botulinum toxin under the definition because it would not materially affect its function and/or objective.

As used herein, the term "about" means approximately or nearly and in the context of a numerical value or range set forth herein means ±10% of the numerical value or range recited or claimed.

The term "treating" includes delaying, alleviating, mitigating, or reducing the intensity, progression, or worsening of one or more attendant symptoms of a disorder or condition and/or alleviating, mitigating, or impeding one or more causes of a disorder or condition. Treatment under the claimed or disclosed inventions may be a preventative treatment, prophylactic treatment, and remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to affect such treatment for the disorder or disease. The "therapeutically effective amount" will vary depending on the composition, the compound, the therapy, the course of treatment, the disorder or disease and its severity and the age, weight, etc., of the individual to be treated. The term "unit" refers to the amount of botulinum toxin needed to kill 50% of a group of 18-20 gm female Swiss-Webster mice given the injection intraperitoneally.

The term "vicinity of a nerve" refers to anywhere on the dermatome involved with the nerve.

In accordance with the principles of embodiments of the present disclosure, use of botulinum toxin to treat diseases of the pancreas or conditions that result in chronic activation of the cytokine system, dysfunction in the central (brain) neural signaling control of the alpha and beta pancreatic cells and neuro excitotoxicity in the beta cells use botulinum toxin.

Cytokines

Cytokines are a diverse group of small proteins and peptides that among other functions regulate and participate in the initial response to infection and tissue damage repair. Some have antibacterial and antiviral properties, some suppress viral and bacterial reproduction, damage DNA, inhibit cell division, some destroy infected cells and tissue, and others raise body temperature to suppress and slow the infection until antibody production begins or cellular damage is removed and repaired.

The major types of cytokines are interferon's, interleukins, chemokines, colony stimulating factors, and tumor necrosing factors. There are hundreds of different peptides under these major classes that damage, kill, or slow the growth of invading bacteria or viruses, and remove or repair damage. They are the body's version of chemotherapy. However, this comes at the cost of some collateral damage. The stronger the cytokine reaction, the more damage to healthy tissue. After the initiating factor is controlled, the cytokine overproduction is slowed and eliminated. The damage to normal tissue is repaired or replaced with fibrous (scar) tissue.

Chronic Pancreatitis

Chronic pancreatitis is the inflammation of the pancreas that can persist even after the initiating factor is eliminated. Over time, the chronic inflammation can lead to permanent damage of the pancreatic tissues. Examples of initiating factors that can cause pancreatitis include but are not limited to smoking, chronic alcohol use, air pollution, toxic substances, and obesity. Studies show it is caused by the chronic, low-grade overproduction of substance P which triggers low grade chronic cytokine production. Symptoms include pain in the upper abdomen that spreads to the back, pain in the belly that gets worse after eating or the consumption of alcohol, diarrhea, nausea and/or vomiting, and possibly weight loss. Symptoms of chronic pancreatitis are treated with medication, such as pain medication, enzymes, insulin, etc. depending on the patient's condition, endoscopic therapies, and sometimes surgery. Success of treatment is dependent on removing underlying causes, severity of condition, and co morbidities. These treatments are minimally effective.

The site of production of the substance P is the neuro structural cells around the sensory ganglia, which chronically produce and release sub-acute levels of substance P and glutamate in the pancreas. The substance P produces a low-grade chronic inflammatory condition that can slowly damage and kill the cells of the pancreas by activating NK receptors on immune cells to stimulate them to produce cytokines. The chronic cytokine production leads to the damage, problems, and symptoms described previously herein.

Diabetes Type II

Blood Glucose Control

The brain is the puppet master of blood glucose level control, using sensory glutamate signaling to the pancreatic beta cells that produce insulin to lower blood glucose levels if too high to avoid neurotoxicity. The brain also decreases substance P signaling to the alpha cells, slowing glucagon production. If blood glucose levels fall too low to maintain the energy needed, then the brain decreases glutamate signaling to the beta cells and increases substance P signaling to the alpha cells that trigger glucagon production to release glucose from the liver and fat cells if needed.

Normal glucose blood levels vary although 80 mg/dl-120 mg/dl is considered normal in general. This is tightly regulated as elevated plasma glucose levels are neurotoxic and low plasma glucose levels cause inadequate energy levels to the brain, muscles, and internal organs—basically the whole body. There is not a constant intake of glucose from food sources and the body energy needs vary from its lowest during sleep to its peak when people are exercising and thinking. The brain consumes lots of energy. It is 4% body weight but uses 25% of the total glucose in a fasting, sedentary individual. When people eat, especially a high sugar or carbohydrate diet, a huge amount of glucose is ingested, and it cannot be released directly into the circulation. This would cause intolerably high blood glucose levels. This problem is solved when all the glucose that is absorbed by the intestines is transported by the hepatic portal vein directly to the liver for processing and release into the bloodstream as needed to maintain proper blood glucose levels. The liver stores the excess glucose to be used to maintain normal levels when not eating. This storage provides for emergencies and varying levels of energy needs of the body. The liver first converts excess glucose into glycogen molecules. Each glycogen molecule contains 200,000-600,000 glucose molecules. The glycogen molecules are stored in the muscles and liver to maintain normal blood glucose levels during the ebb and flow of demand. There is a saturation level in this storage capacity of the liver and muscles for short-term energy use. If there is excess glucose after storage capacity is reached, it is converted to fatty acid and sent through the bloodstream to the fat cells for storage. Fat is broken down to glucose if dietary glucose intake does not match glycogen depletion from the liver and muscles.

Fats are digested and processed in the intestines and enter the bloodstream through normal circulation instead of the hepatic portal vein as with carbohydrates and sugars. The liver transfers excess fat to the fat cells in the form of cholesterol.

The liver closely communicates with the adipose (fat) tissues and skeletal muscle tissues through multiple mechanisms to balance the food intact, energy storage system, supply of energy on hand for ordinary uses or sudden emergencies. Excess fat is stored in hepatocytes intracellularly in droplets. Some is processed to be used structurally in cells.

Liver metabolic processes are regulated by neural and hormonal systems. The sympathetic spinal neurons (T-5>L-3), and the vagus nerves are involved in the neural control of the glucose levels. When the brain detects higher than normal glucose levels, it sends intraneural glutamate signals via these nerves to the pancreatic beta cells which then secrete insulin to lower glucose release from the liver to maintain proper blood glucose levels. There are also glutamate receptors on the exterior of beta cells that react to extracellular glutamate. Increased insulin decreases blood glucose levels, and decreased insulin production increases blood glucose levels. There are numerous other proteins and receptors that fine tune the system such as growth hormone, cytokines, G.I. hormones, etc.

When the brain detects too low blood glucose level, it sends substance P intraneural signals to the alpha pancreatic cells. The alpha cells produce and release into the bloodstream a hormone called glucagon. This has the opposite effect of insulin. When glucagon reaches the liver, it induces glycogen breakdown and release of glucose into the blood. Glucagon also induces fat cells to release glucose through the breakdown of stored fat. There are substance P receptors on the exterior of the alpha cells.

Current treatments for diabetes include insulin, blood sugar monitoring, diet and exercise, Metformin, statins to improve cholesterol, SGLT2 inhibitors, transplantation, bariatric surgery, artificial pancreas, and pancreatic islet transplantation with greater or lesser results depending on patient compliance and progress of the condition.

The chronic substance P production in chronic pancreatitis from the neuro structural cells of the sensory ganglia can cause direct damage to the alpha and beta cells that are involved with glucose regulation by the cytokine production it induces in the immune cells. This in itself is harmful, but it has another more far-reaching effect. The excess chronic glutamate and substance P production can disrupt the whole glucose control mechanism. The excess substance P stimulation of the alpha cells produces a constant overproduction of glycogen releasing glucose from the liver and fat cells. This mechanism is beyond central brain control. The brain senses the rising blood levels of glucose and stops intraneural substance P signaling to the alpha cells which is ineffective because the substance P is coming from this alternative source. This is called insulin resistance. The brain also increases glutamate signaling to the beta cells to produce more insulin. The beta cells ramp up insulin production. This temporarily controls blood glucose.

However, the alpha cells are not inhibited from producing glucagon because of the non-centrally produced substance P. The beta cells must work constantly to produce insulin in ever-increasing amounts in an attempt to control blood glucose levels. This constant glutamate stimulation causes a serious problem for the beta cells. They are neuron-type cells and constant firing produces a condition called neuro excitotoxicity. A constant influx of Ca ions from the constant excitation creates a pH imbalance in these neuron-like cells. This causes the beta cells' apoptosis mechanism to engage with resulting cell damage and death. As the beta cells die, there is more work for the remaining ones and a cascade of beta cell death causes inadequate insulin production, allowing neurotoxic levels of glucose in the blood.

Diabetes Treatment

The body's glucose regulation system is a good, quick-acting system that supplies constant, adequate but not toxic level of glucose to the body. However, things can go wrong with the neural signaling system in the pancreas. The neural injury mechanism that is involved in sensing and fighting infection from the neuro structural cells can become chronically over activated resulting in dysfunction in this system. The neural structural cells (astrocytes, glial, satellite) around the dorsal root ganglia and vagal ganglia cells produce chronic excess levels of substance P, glutamate, and CGRP. The excess substance P triggers the immune response, stimulating immune cells to release cytokines. This also causes non centrally controlled signaling to the alpha cells to produce an uncontrolled release of glycogen. In the beta cells, it causes excess stimulation. This increases insulin production but ultimately beta cells die by neuro excitotoxicity. Elimination of the exogenous substance P and glutamate will help restore normal central neural control of the blood glucose levels. If a large percentage of beta cells is destroyed by neuro excitotoxicity, then supplemental insulin may be needed to maintain proper blood glucose control damage. However, several studies show alpha cells have the capacity to change into beta cells. This could happen without the chronic inflammatory environment and excess glutamate-induced overstimulation of the new beta cells.

Chronic low-grade overproduction of substance P and glutamate have been shown to be able to be controlled by the use of subcutaneous botulinum toxin injections in other conditions such as COPD. Botulinum toxin given subcutaneously in the involved dermatomes and other dermatomes that may be overproducing substance P and glutamate should mitigate or stop the excess substance P and glutamate overproduction from the neuro structural cells. This should restore central control of the blood glucose levels and mitigate or control diabetes type II.

Clinical Treatment of Pancreatitis and Diabetes Type II

If a patient is diagnosed with chronic pancreatitis and/or diabetes type II caused by overproduction of substance P and glutamate with the resulting chronic cytokine production, chronic interference of the normal, centrally controlled glucose regulation system, and needs treatment thereof. Botulinum toxin can be given in the needed dermatomes. This may encompass T-3 to L-1 or all dermatomes, if necessary. It will take approximately 5-14 days for the botulinum toxin to stop the overproduction of substance P and glutamate and mitigate or control chronic pancreatitis and/or diabetes.

1) In embodiments of the present disclosure, a patient diagnosed to experience chronic pancreatitis, diabetes type II, or other conditions that have resulted in excess activation of the cytokine system in the pancreas can be given botulinum toxin subcutaneously or by any other injection that allows the botulinum toxin to reach the unmyelinated sensory C fiber (e.g., intradermal injection, etc.) to prevent or alleviate elevated levels of substance P and glutamate. The sensory innervation of the pancreas comes from the vagus nerve and spinal nerves, T-6 to L-2, the botulinum toxin injection can be given to and/or around the vicinity of a trigeminal nerve, a cervical nerve, a thoracic nerve, a lumbar nerve, a sacral nerve, or a combination thereof of the patient. Preferably, it is not necessary to inject botulinum toxin to the vagus nerves because there are numerous anastomoses between the trigeminal nerves and the spinal nerves. The selected trigeminal nerve may include, but is not limited to, an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof. In the facial dermatome, botulinum toxin is injected subcutaneously to the trigeminal nerve or around the vicinity of the trigeminal nerve because the trigeminal nerve is entirely sensory. In contrast, the facial nerve supplies motor innervations to the face and has no subcutaneous axons. Thus, injecting botulinum toxin to the trigeminal nerve minimizes or eliminates muscular side effects. The selected cervical nerve may include, but is not limited to, the c-2 nerve, c-3 nerve, c-4 nerve, c-5 nerve, c-6 nerve, c-7 nerve, c-8 nerve, or a combination thereof. The selected thoracic nerve may include, but is not to, the t-2 to t-3 nerve, t-1) to t-6 nerve, t-7 to t-9 nerve, and/or t-10 to t-12 nerve, or a combination thereof. The selected lumbar nerve may include, but is not limited to, the l-1 to l-2 nerve, l-2 to l-3 nerve, and/or l-4 to l-5 nerve, or a combination thereof. The selected sacral nerve may include, but is not limited to, the s-1 to s-2, s-3 to s-4, and/or s-4 to s-5, or a combination thereof. For example, 1-4 units to and/or around the vicinity of an ophthalmic, maxillary, and/or mandibular nerve of the trigeminal nerve (bilateral), 1-4 units to and/or around the vicinity of the c-2 to c-3, c-4 to c-6, and/or c-7 to c-8 of the cervical nerve, about one-inch lateral to the patient's spine (bilateral), 1-4 units to and/or around the vicinity of the t-2 to t-3, t-5 to t-6, t-7 to t-9, and/or t-10 to t-12 of the thoracic nerve, about one inch lateral to the patient's spine (bilateral), 1-4 unit to and/or around the vicinity of the l-1 to l-2, l-2 to l-3, and/or l-4 to l-5 of the lumbar nerve, about one inch lateral to the patient's spine (bilateral), and/or 1-4 units to and/or around the vicinity of the s-1 to s-2, s-3 to s-4, and/ or s-4 to s-5 of the sacral nerve, about one inch lateral to the patient's spine (bilateral) can be administered. While the administration site is about one-inch lateral to the patient's spine in the above embodiment, the distance can be more than 0 inches, about 0.1-3 inches, about 0.5-2.5 inches or about 1.0-2.0 inches. Alternatively, the distance can be about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0 inches. The methods according to embodiments of the present disclosure are preferably applied to all or many of these locations. Depending on symptoms or conditions, the botulinum toxin used in embodiments of the present disclosure be injected to a subset or subgroup of the locations described in embodiments of the present disclosure. In one embodiment, 3 injections of 2 units each distributed along each side of the neck in the cervical area on the trigeminal nerve, 1 injection of 2 units in the ophthalmic, maxillary, mandibular division subcutaneously and bilaterally. These dosages are for an adult who weighs about 150 lbs. The dosage for an adult or a child with asthma would have to be adjusted for age, weight, or a combination thereof.

The sites of injection and dosage according to embodiments of the present disclosure are novel and inventive as they allow for a minimal amount of botulinum toxin to be injected and still cover all dermatomes with no or minor motor involvement. By using a subcutaneous or intradermal injection that reaches the unmyelinated C-fibers, it takes less botulinum toxin to absorb into them as opposed to the myelinated nerves, and there are no motor nerves in the epithelium. Also, the injection site ½ to 1 inch from the patient's spine allows for a lower dose of botulinum toxin because there is a shorter distance to the dorsal root ganglia (approximately ¼ inch) for botulinum toxin to diffuse as compared to several feet if given in the arm or leg. The site is the only place in the body where the sensory and motor nerves are not in close proximity. This combination of low dose and separation of approximately 1 inch of bone and tissue between the motor and sensory nerves should. minimize or eliminate any motor side effects Furthermore, the methods according to embodiments of the present disclosure do not require vagus nerve injection. The only superficial exposure of the vagus nerve is Arnold's nerve which is in the ear canal. It is a mixed motor and sensory nerve, and the motor component of it innervates the throat. If you inject botulinum toxin to or around the Arnold's nerve, you can generate speech and swallowing problems. The inventor has found that there is enough anastomosis between the sensory cervical nerves, the trigeminal nerve and the vagus nerve that botulinum toxin can reach the vagus ganglia and stop the overproduction of substance P, glutamate, and CGRP by anastomosis due to interconnections between the cervical and trigeminal nerves and the sensory components of the vagus nerve.

Botulinum toxin is given to lower the levels of substance P and glutamate to normal levels. It normally begins to work in 5-14 days.

In general, the total dosage or amount can be, for example, 1-150 units depending on the patient's body weight. For adults or a child, the dosage can be adjusted to the patient's body weight, age, or a combination thereof. The therapeutically effective amount can be about 1 to about 50 units, about 1 to about 30 units, about 50 to about 100 units, about 1 to about 60, about 6 to about 60, and about 50 to about 150.

Botulinum toxin is given to lower the levels of substance and glutamate, and botulinum toxin normally begins to work after about three days. It normally takes the botulinum toxin about one to two weeks to reach the height of its effectiveness. Physical symptoms can be monitored, and blood tests drawn to assess substance P levels to make sure these levels return to normal, When the botulinum toxin wears off and symptoms return, blood tests show an increase in substance P, glutamate, or an elevation of blood glucose levels. More botulinum toxin can be given to combat the symptoms of the condition. Clinical Observation shows the effect will last approximately 2 months.

For patients, as discussed, it is possible to use the claimed method to delay, alleviate, mitigate or reduce the intensity, progression, or worsening of one or more attendant symptoms of a disorder or condition, and/or the claimed method alleviates, mitigates or impedes one or more causes of these disorders or conditions.

Botulinum toxins for use according to embodiments of the present disclosure can be stored in lyophilized, vacuum dried form in containers under vacuum pressure or as stable liquids. Prior to lyophilization, the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Preferably, the botulinum neurotoxin is peripherally administered by administering it to or in the vicinity of the nerve or to the aforementioned nerve branch or its ganglion nuclei. This method of administration permits the botulinum neurotoxin to be administered to and/or to affect select intracranial target tissues. Methods of administration include injection of a solution or composition containing the botulinum neurotoxin, as described above, or could include implantation of a controlled release system that controllably releases the botulinum neurotoxin to the target trigeminal tissue. Such controlled release systems reduce the need for repeat injections. Diffusion of biological activity of botulinum toxin within a tissue appears to be a function of dose and can be graduated. Jankovic J., et al *Therapy with Botulinium Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder and does not have negatively adverse effects on other neural systems.

In addition, the botulinum neurotoxin may be administered to the patient in conjunction with a solution or composition that locally decreases the pH of the target tissue environment. For example, a solution containing hydrochloric add may be used to locally and temporarily reduce the pH of the target tissue environment to facilitate translocation of the neurotoxin across cell membranes. The reduction in local H may be desirable when the composition contains fragments of botulinum neurotoxins that may not have a functional targeting moiety (e.g., a portion of the toxin that binds to a neurotoxin receptor, and/or a translocation domain). By way of example, and not by way of limitation, a fragment of botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its effects within the cell. The pH of the target tissue is only temporarily lowered so that neuronal and/or glial injury is reduced.

The botulinum toxin used in the treatment in accordance with embodiments of the present disclosure comprises botulinum toxin type A, botulinum toxin type B, botulinum toxin type C, botulinum toxin type D, botulinum toxin type E, botulinum toxin type F, botulinum toxin type G, a fragment thereof, a hybrid thereof, a chimera thereof, or a combination thereof. Because of different mechanisms and cleavage sites of botulinum toxins, the potency, dosage, or duration may vary depend on the type of botulinum toxins. The botulinum toxin can be used with other modulating drugs or chemicals. In further embodiments, the therapeutically effective amount of the botulinum toxin administered is between about 1 unit and about 150 units.

In some embodiments, a composition administered to a patient consists of botulinum toxin(s).

In some embodiments, a pharmaceutically active composition contained in a composition administered to a patient consists of botulinum toxin(s). The composition may additionally include, but not be limited to, a pharmaceutically inactive excipient, stabilizer and/or carrier.

In some embodiments, a composition administered to a patient consists essentially of botulinum toxin(s). The language "consists essentially of" excludes materials (that contribute to the treatment) that materially mitigate cytokine overproduction and thereby affecting the treatment of pancreatitis, diabetes type II, and other conditions that have resulted from the overproduction of cytokines in the pancreas.

In some embodiments, a composition administered to a patient botulinum toxin(s). The composition may further comprise one or more additional pharmaceutically active ingredients. The composition may further comprise one or more additional pharmaceutically inactive ingredients.

If lyophilized botulinum toxin may be reconstituted with saline or water o make a solution or composition to be administered to the patient.

In some instances, the therapeutically effective amount can be about 1 (or 2) to about 4 units.

Diabetes Type II Case Study

The following is a case study of a 57-year-old female. She had been treated for diabetes for 18 years and struggled with control. She had received insulin injections 1-3×/day, Trajenta 5 mg 1×/day and Starlix 3×/day.

On Jan. 15, 2021, she received botulinum toxin using the injection technique described in embodiments of the present disclosure (cervical, thoracic, lumbar, sacral, and trigeminal dermatomes). 10 days later, she stopped her insulin injections because her blood glucose was too low. After 2 weeks, she stopped taking Trajenta and started taking only Starlix 2×/day. Her doctor said in June to stop Starlix altogether, and she did so. She has received only botulinum toxin every 8 weeks to maintain control of her diabetes.
Further patient testing is being pursued using botulinum toxin.

The description of ranges also describes the ranges within the specifically described range and describes individual numerical points for treatment. The described ranges are inclusive of endpoints in the range.

It should be understood that the present description of embodiments of the invention includes a composition for use in treating the conditions. For example, botulinum toxin for use in treating chronic pancreatitis and/or diabetes type II in a patient in a need thereof.

It should be understood that the above description of embodiments of the invention and specific examples, while indicating preferred embodiments of the present invention, are given by way of illustration and not limitation. Many changes and modifications within the scope of the present invention may be made without departing from the spirit thereof, and the present invention includes all such changes and modifications.

What is claimed is:

1. A method for treating chronic pancreatitis and/or diabetes type II using botulinum toxin, in a patient in need thereof, comprising administering botulinum toxin to the patient, thereby treating chronic pancreatitis and/or diabetes type II, wherein the patient is administered by subcutaneous or intradermal injection, 1-4 units to and/or around the vicinity of a trigeminal nerve, 1-4 units to and/or around the vicinity of a cervical nerve, lateral to the patient's spine, 1-4 units to and/or around the vicinity of a thoracic nerve, lateral to the spine, 1-4 units to and/or around the vicinity of a lumbar nerve, lateral to the spine, and/or 1-4 units to and/or around the vicinity of a sacral nerve, lateral to the spine.

2. The method of claim 1, wherein the trigeminal nerve comprises an ophthalmic nerve, maxillary nerve, mandibular nerve, supraorbital nerve, supratrochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve, a greater occipital nerve, or a combination thereof.

3. The method of claim 1, wherein the cervical nerve comprises a c-1 nerve, c-2 nerve, c-3 nerve, c-4 nerve, c-5 nerve, c-6 nerve, c-7 nerve, c-8 nerve, or a combination thereof.

4. The method of claim 1, wherein the thoracic nerve comprises a t-1 nerve, t-2 nerve, t-3 nerve, t-4 nerve, t-5 nerve, t-6 nerve, t-7 nerve, t-8 nerve, t-9 nerve, t-10 nerve, t-11 nerve, t-12 nerve, or a combination thereof.

5. The method of claim 1, wherein the lumbar nerve comprises a 1-1 nerve, 1-2 nerve, 1-3 nerve, 1-4 nerve, 1-5 nerve, or a combination thereof.

6. The method of claim 1, wherein the sacral nerve comprises an s-1 nerve, s-2 nerve, s-3 nerve, s-4 nerve, s-5 nerve, or a combination thereof.

7. The method of claim 1, wherein the botulinum toxin comprises botulinum toxin type A, botulinum toxin type B, botulinum toxin type C, botulinum toxin type D, botulinum toxin type E, botulinum toxin type F and botulinum toxin type G, a fragment thereof, a hybrid thereof, a chimera thereof, or a combination thereof.

8. The method of claim 1, wherein each of the subcutaneous or intradermal injection is bilateral.

9. The method of claim 1, wherein a total dosage of the botulinum toxin for an adult who weighs about 150 lbs. is between about 1 unit and about 150 units.

10. The method of claim 1, wherein a total dosage of the botulinum toxin for an adult or a child is adjusted for age, weight, or a combination thereof.

11. The method of claim 10, wherein the total dosage contains therapeutically effective amount of botulinum toxin.

12. The method of claim 11, wherein the therapeutically effective amount is 1-50 units.

13. The method of claim 12, wherein the therapeutically effective amount is 1-30 units.

14. The method of claim 13, wherein the therapeutically effective amount is 1-4 units.

15. The method of claim 14, wherein the therapeutically effective amount is 2-4 units.

16. The method of claim 1, wherein each of the injections is 2-4 units.

17. The method of claim 1 further comprises monitoring a physical symptom, a blood glucose level and/or a neuroexcitatory substance level from the patient.

18. The method of claim 17, wherein the neuroexcitatory substance comprises substance P, calcitonin gene-related peptide (CGRP) or glutamate.

19. The method of claim 17 further administering additional botulinum toxin to the patient if the physical symptom, the blood glucose level and/or the neuroexcitatory substance level fails to normalize.

20. The method of claim 1, wherein botulinum toxin is the only pharmaceutically active ingredient for the treatment.

* * * * *